United States Patent [19]

Johnson

[11] 4,067,336
[45] Jan. 10, 1978

[54] PERINEAL SHIELD AND DISCHARGE CONTAINMENT DEVICE

[75] Inventor: Russell L. Johnson, Weyauwega, Wis.

[73] Assignee: Kimberly-Clark Corporation, Neenah, Wis.

[21] Appl. No.: 726,964

[22] Filed: Sept. 27, 1976

[51] Int. Cl.² ............................................. A61F 13/16
[52] U.S. Cl. ...................................... 128/284; 128/287
[58] Field of Search ............... 128/287, 290 R, 290 P, 128/290 B, 284, 288

[56] References Cited

U.S. PATENT DOCUMENTS

| | | | |
|---|---|---|---|
| 1,451,643 | 4/1923 | Woody | 128/284 |
| 1,958,082 | 5/1934 | Ellinger | 128/284 |
| 2,059,956 | 11/1936 | MacGlashan | 128/284 |
| 2,829,647 | 4/1958 | Dexter | 128/284 |
| 3,968,799 | 7/1976 | Schrading | 128/287 |
| 3,978,861 | 9/1976 | Schaar | 128/287 |

*Primary Examiner*—Lawrence W. Trapp
*Attorney, Agent, or Firm*—Daniel J. Hanlon, Jr.; William D. Herrick; Raymond J. Miller

[57] ABSTRACT

A protective and discharge containment device for the perineum made from flexible sheet material shaped to provide close conformity with changing perineal contours by being folded on a set of pre-established lines radiating outward from a base point interiorly disposed on a line defining the main longitudinal axis of the sheet material. When folded as prescribed, the sheet material takes on an upwardly concave configuration in both the transverse and longitudinal directions with the deepest part of the concavity originating at the base point. The folded sheet material when positioned on the perineum provides an upstanding anterior portion comprising the full width of the sheet which covers and conforms to the pubic area, then tapers down to an adjacent narrow isthmus which fits comfortably between the thighs, and a rearwardly diverging posterior portion which covers and conforms to the remaining perineal area and is free to bend, twist and pivot around the base point and to flex up and down along the main fold, and thereby readily adjust to whatever movement the protected body area may make in the course of normal daily activities.

25 Claims, 18 Drawing Figures

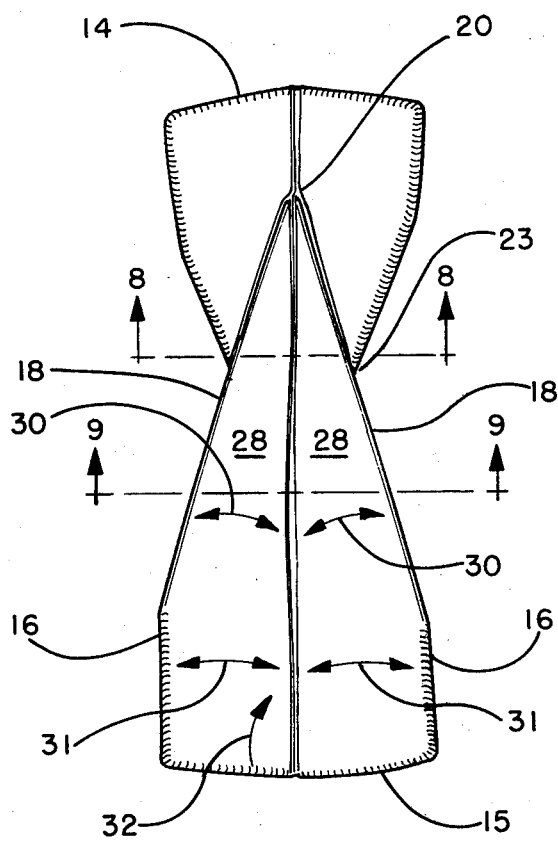 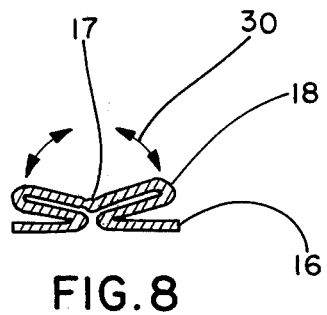 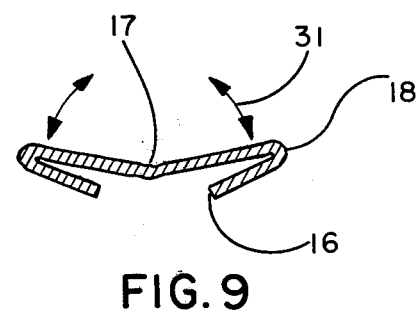 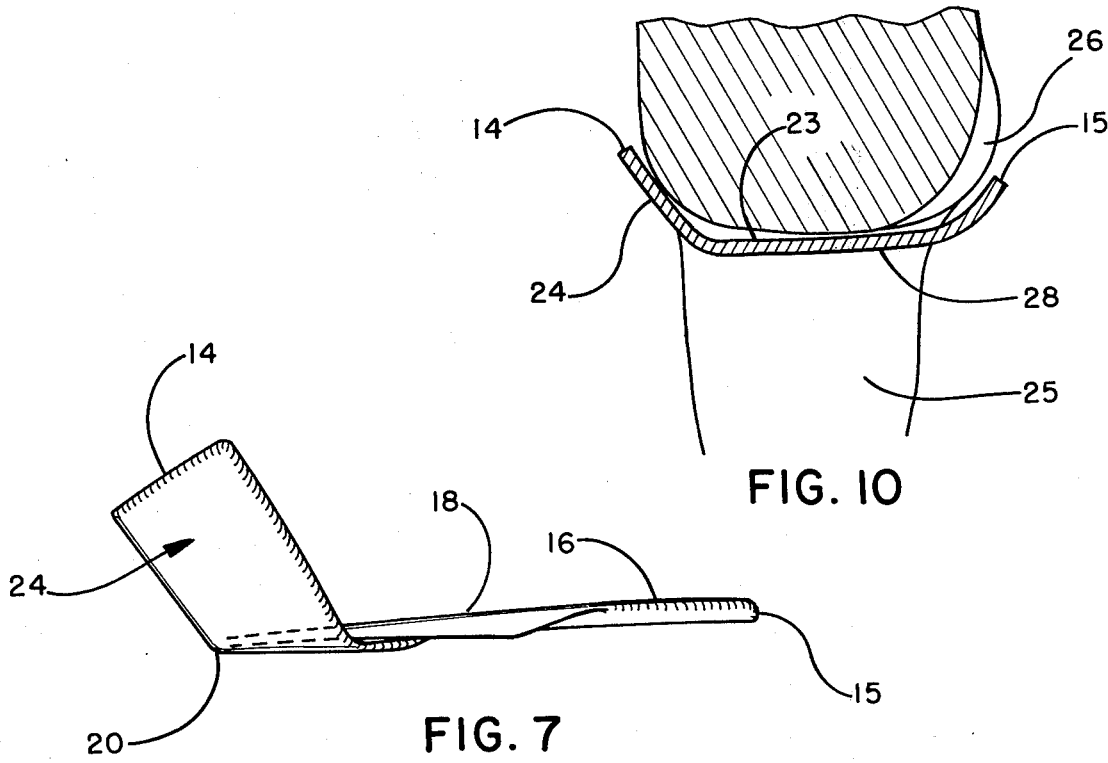
FIG. 6  FIG. 8  FIG. 9  FIG. 10  FIG. 7

PERINEAL SHIELD AND DISCHARGE CONTAINMENT DEVICE

BACKGROUND OF THE INVENTION

The prior art is replete with structures relating to perineal protective devices including such items as garment shields, drip containment or dribble cups, sanitary napkins, diapers, incontinent pads and the like. Such devices range from very thin material for protecting against garment stains which might otherwise result from small amounts of involuntary fluid discharge, to pads having sufficient capacity to absorb the full flow of menstrual fluid discharge, to still heavier pads for infant diapering and for collecting, absorbing and retaining the entire discharge of adult incontinence.

Various shapes have been devised in an attempt to obtain good body conformance, leakage prevention, and comfort. While many are designed for re-use and are made from launderable fabrics, the most recent developments have been directed to disposable materials including non-woven webs, thin plastic films, and thick pads of absorbent fibers, in particular air-formed pads of wood cellulose fibers. A major difficulty with most of the disposable materials is that they do not have the drapability of more permanent cloth-like material and therefore will not conform well to the body, especially when made thick enough to provide the absorbent capacity needed for catamenial and diapering uses.

Various attempts have been made to obtain conformity by selecting particular fold geometries. While many of these obtain a good fit when first applied, they do not have the ability to move with changing body configurations. As a result, the material located between theh thighs is often crushed by leg pressure soon after application, and thereby loses it initial conformance, resulting in gaps between the protective device and the body, or causing discomfort because of rubbing and/or chafing contact between the device and the body.

The invention disclosed herein is directed to a perineal protective device made from flexible sheet material which when folded on a set of pre-established lines assumes a self-adjusting, body-conforming shape, achieving improved comfort and containment characteristics while being well-suited for all size devices ranging from the above-mentioned relatively thin garment protectors to absorbent pads which handle full-discharge incontinents.

SUMMARY OF THE INVENTION

This invention is directed to a perineal shield and discharge containment device comprised of a sheet of flexible material of generally rectangular form adapted for folding on a set of pre-established fold lines. The sheet material is generally defined by a top body-contacting surface, a bottom surface, a front edge, a back edge, and two side edges. The pre-established fold lines along which the sheet material is folded prior to use comprise: (a) a main fold line centrally and longitudinally disposed along the major axis of the sheet and extending the full length of the sheet; (b) a first pair of rearwardly directed diverging fold lines originating on the main fold line from a common base point spaced inwardly from the front edge of the sheet, and extending to the sheet perimeter; and (c) a second pair of rearwardly directed diverging fold lines disposed between the first pair of diverging lines and the side edges of the sheet, with the second pair of lines also originating at the same common base point on the main fold line as the first set of lines and extending to the sheet perimeter.

The sheet material is adapted for inward folding on the main fold line, outward folding on the first pair of rearwardly diverging lines, and inward folding on the second pair of rearwardly diverging lines.

When folded as prescribed, the sheet material has an upwardly concave or bent configuration in both the transverse and longitudinal directions. The deepest part or greatest depth of the concavity in both directions originates at the above-mentioned common point on the main fold line.

When the folded sheet material is positioned against the perineal area between the thighs it provides an upstanding anterior portion traversing the full width of the sheet which covers and conforms to the public area then tapers downward to a narrow isthmus-like section which fits between and conforms to the thighs and due to the folded arrangement is capable of flexing in and out without crushing, and a rearwardly diverging posterior portion which covers and conforms to the remaining perineal area and is free to move and adjust to movements of the contacted body parts.

Other features, objects and advantages of the invention will become apparent by reference to the accompanying drawings and the detailed description which follows.

BRIEF DESCRIPTION OF THE DRAWINGS

In the drawings:

FIG. 6 is a top plan view of the folded sheet material of FIG. 5.

FIG. 7 is a side view of the folded sheet material of FIG. 6.

FIG. 8 is a sectional view taken along line 8—8 of FIG. 6.

FIG. 9 is a sectional view taken along line 9—9 of FIG. 6.

FIG. 10 is a partial front-to-back sectional and diagrammatic view of the perineal area of a human body with the FIG. 7 folded sheet material in place.

DETAILED DESCRIPTION OF THE PREFERRED EMBODIMENTS

FIGS. 1 – 5 show a series of perspective views of a sheet of flexible material having pre-established fold lines in accordance with the invention, first in its unfolded condition and then followed by sequential folding to a fully folded condition ready for use.

Figure 1:
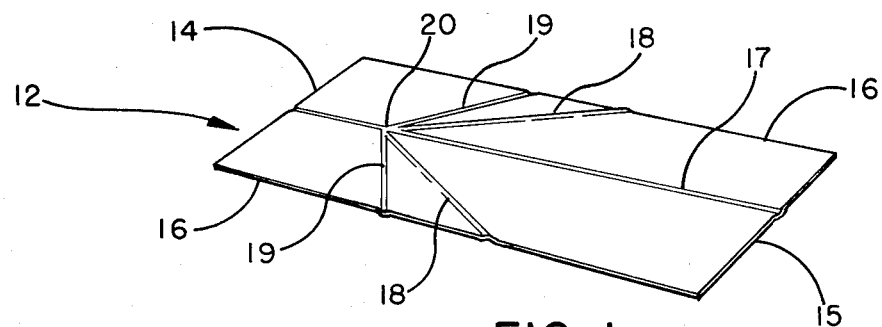
FIG. 1 is a top perspective view of a rectangular sheet material showing the arrangement of the pre-established fold lines of this invention.

In FIG. 1, an elongate rectangular sheet of material 12 having a front edge 14, a back edge 15 and two side edges 16 is provided with a multiplicity of fold lines including a main fold line 17 centrally and longitudinally disposed along the major axis; a first pair of rearwardly diverging fold lines 18 originating on main fold line 17 from a common base point 20 spaced inwardly from front edge 14 and extending to the sheet perimeter at side edges 16; and a second pair of rearwardly diverging fold lines 19 also originating from base point 20 and disposed in spaced arrangement between the first pair of diverging lines 18 and side edges 16 and terminating at side edges 16.

Figure 2:
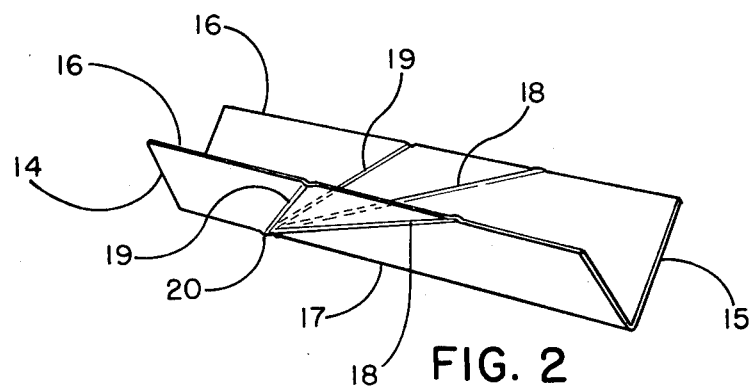
FIGS. 2 – 4 are perspective views showing the sequential folding of the sheet material along the pre-established fold lines.
Figure 3:
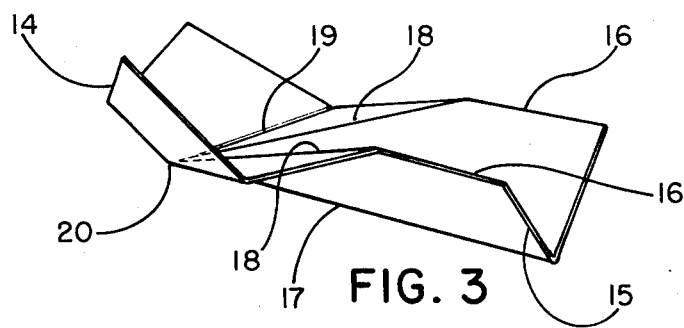

In the folding sequence, FIG. 2 shows the sheet being folded inwardly on main line 17, FIG. 3 shows the sheet being folded outwardly on the first pair of rearwardly diverging lines 18 and folded back inwardly on the second pair of rearwardly diverging lines 19.

Figures 4, 5:
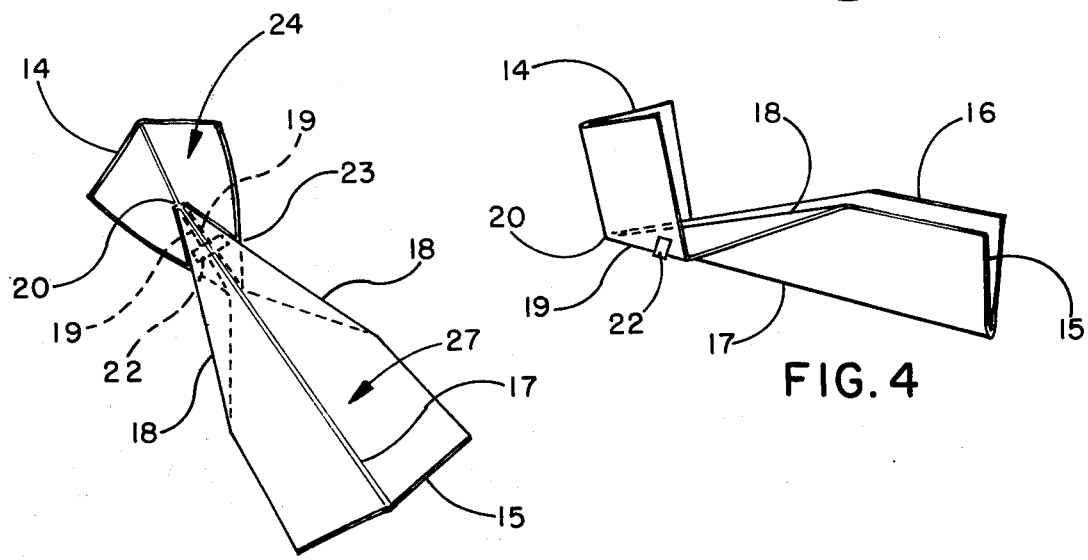
FIG. 5 is a top perspective view of the folded sheet material partially re-opened and ready for positioning on the body.

In FIG. 4, the sheet is completely folded and as shown therein may be secured in its folded condition by securement means disposed adjacent the first pair of diverging fold lines. The securement means may optionally be a short strip of tape 22 which stretches across the second pair of fold lines 19, or the securement means may comprise a spot or spots of hot melt, pressure sensitive, or other adhesive disposed between facing planar surfaces adjacent the folds, as shown at 13 in FIGS. 11 and 12. Double faced adhesive tape is also suitable for this purpose as are various mechanical fasteners.

In FIG. 5, the folded sheet of FIG. 4 has been partially reopened to expose the top surface to illustrate the configuration which the protective device assumes as it is readied for positioning on the perineum. As shown therein the partially opened device has an upstanding frontal portion 24 which comprises the full width of the sheet and angles upward from base point 20, a narrow isthmus-like portion 23 disposed between base point 20 and back edge 15, and an outwardly and rearwardly diverging anterior portion 27 originating at base point 20.

As viewed in this form and in more detail in FIGS. 6 – 9, the folded device has a concave longitudinal configuration with the base of the concavity at base point 20, being bent upward from that point toward both the front and back, while also having a concave transverse configuration with a base or valley along main fold line 17. The effect is to provide a pouch or cup at the front portion of the device, which bottoms out at base point 20 and functions as a primary containment area.

As shown in FIG. 6 and sectional FIGS. 8 – 9, the rearwardly diverging anterior portion of the sheet comprises two triangular panels 28 the planar surfaces of which angle transversely upward from main fold line 17 and have a common forward apex at base point 20. Each of these panels is free to move up and down from main fold line 17 and apex 20 in the directions indicated by arrows 30, 31 and 32. The advantage of this capability may be better understood by reference to FIG. 10 in which the folded protective device is shown in position over the perineal area. As shown therein, frontal upstanding portion 24 is in snug association with the pubic area. The narrow isthmus-like section 23 is located centrally of the inner thighs 25 where the thighs are normally in closest proximity, and the triangular anterior panel 29 is in contact with the buttocks 26. As is well known, the gluteal muscles of the buttocks on either side of the perineum move alternately up and down during normal walking activity. Since anterior portions 28 of the protective device are free to move up and down from pivot point 20 and along main fold 17, the device readily conforms to the body movement without disturbing the relatively immovable association of frontal panel 24 with the pubic area which area is normally relatively stationary with respect to the moving gluteal muscles. Rubbing movement between the device and the surface of the body it contacts is thereby substantially eliminated. The fold arrangement at the thighs also permits the pad to expand or contract by angular motion at the folds in response to leg pressure without crushing and thereby eliminate another source of discomfort and/or poor fit.

A large variety of shapes and sizes for the basic sheet material, as well as the angular relationships of the rearwardly diverging fold lines are possible without departing from the advantages of this invention. Some of these latter variations are shown in FIGS. 11 – 18.

Figure 11:
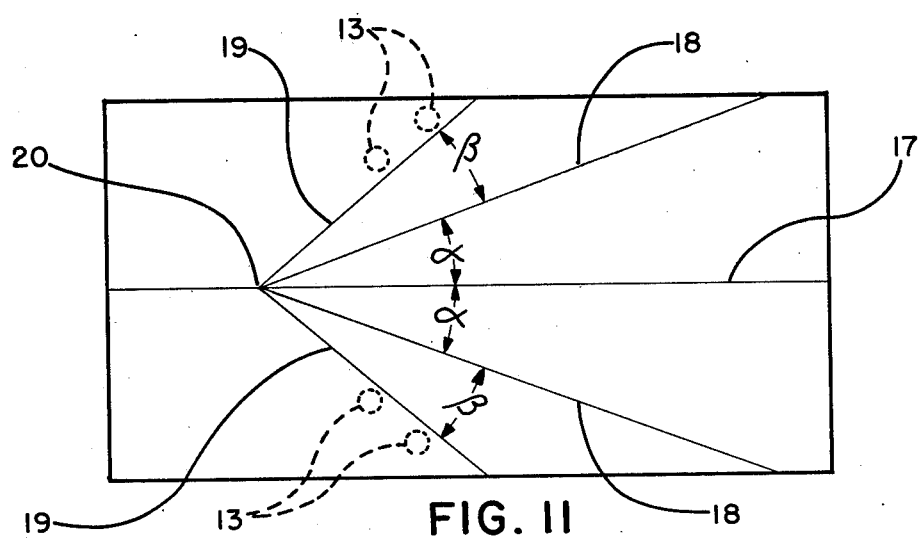
FIG. 11 is a plan view of a rectangular sheet showing an arrangement of fold lines similar to FIG. 1.
Figure 12:
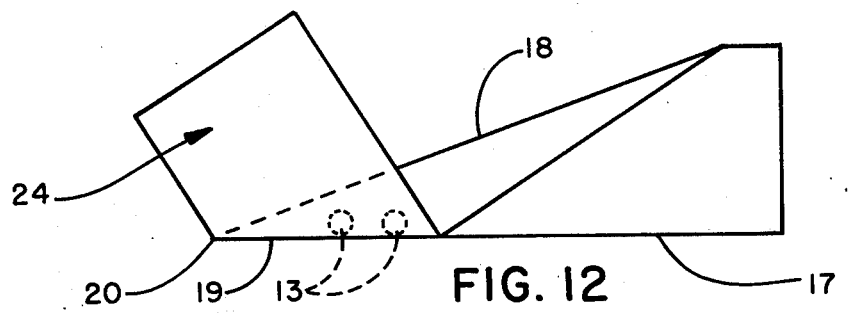
FIG. 12 is a side view of the FIG. 11 material after folding on the pre-established fold lines.

In FIGS. 11 – 12 the angle $\alpha$ between main fold line 17 and the first pair of outwardly diverging fold lines 18 is equal to angle $\beta$ between the first pair of outwardly diverging fold lines 18 and the second pair of outwardly diverging fold lines 19.

When this arrangement is folded, fold line 19 lies along main fold line 17.

Figure 13:
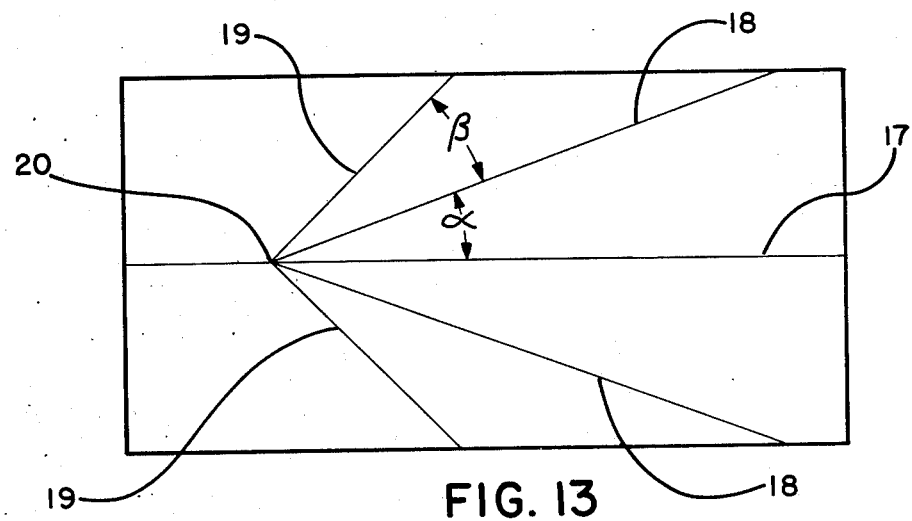
FIG. 13 is a plan view showing another arrangement of fold lines.
Figure 14:
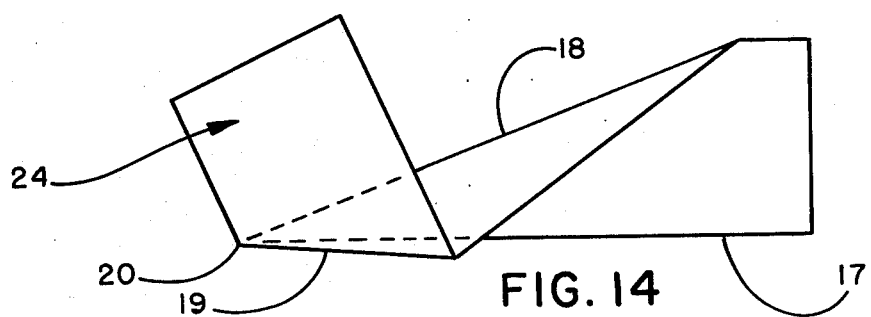
FIG. 14 is a side view of the FIG. 13 embodiment after folding.

In FIGS. 13 – 14 where angle $\alpha$ is less than angle $\beta$, fold line 19 falls below main fold line 17 and the anterior portion 24 of the device moves closer to the perpendicular.

Figure 15:
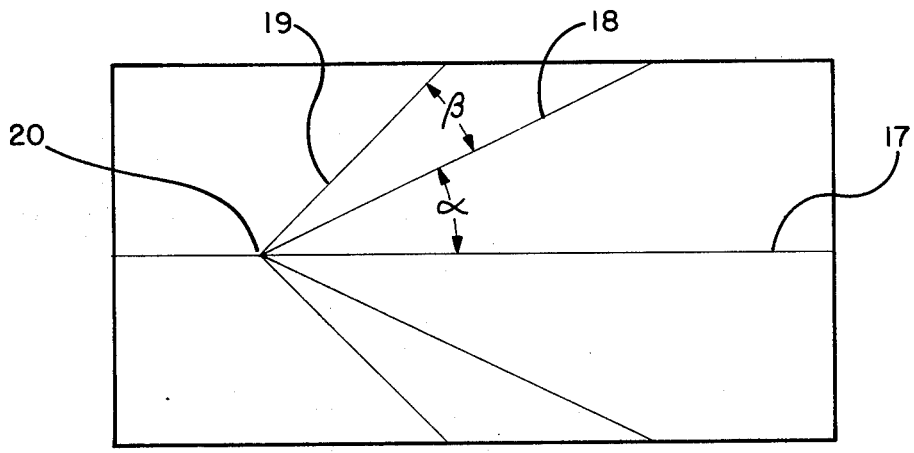
FIG. 15 is a plan view showing still another arrangement of fold lines.
Figure 16:
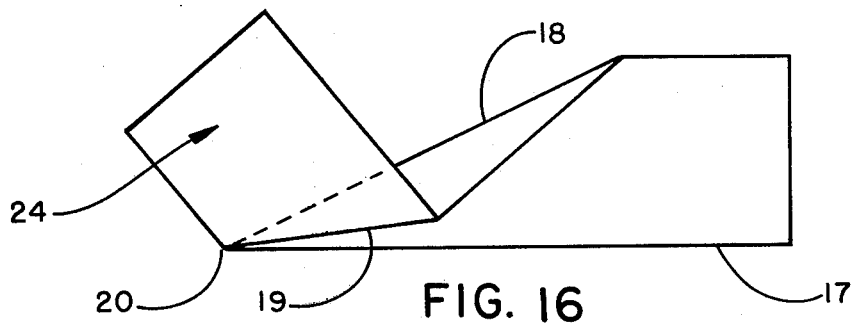
FIG. 16 is a side view of the FIG. 15 embodiment after folding.

In FIGS. 15 – 16 where angle $\alpha$ is greater than angle $\beta$, fold line 19 falls above fold line 17 and the anterior portion 24 of the device moves closer to the horizontal.

Thus by adjusting the relationship between angular disposition of the rearwardly diverging fold lines, one may conveniently adjust the upward angularity of the anterior panel of the device to conform to various body configurations.

As the drawings indicate, angles $\alpha$ and $\beta$ are always acute angles, whether they are equal or not. A preferred range of angularity is from about 12° to about 30°.

Figure 17:
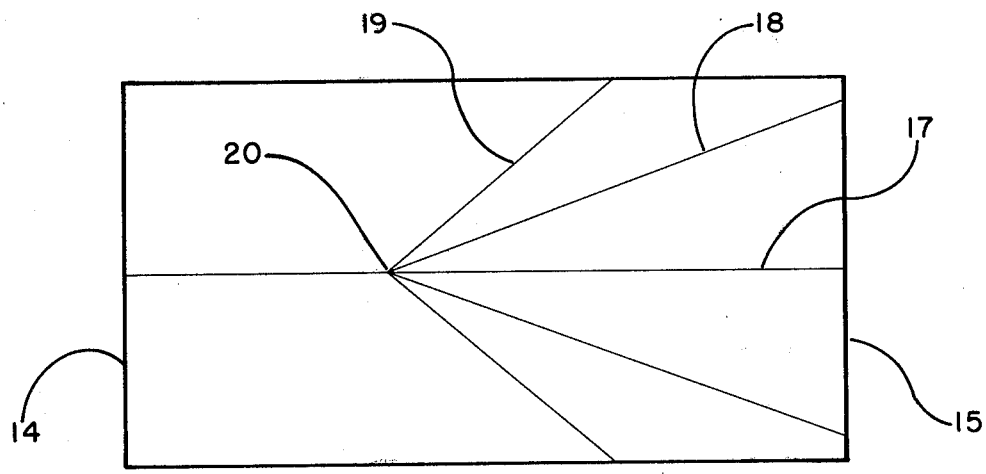
FIG. 17 is a plan view showing yet another arrangement of fold lines.
Figure 18:
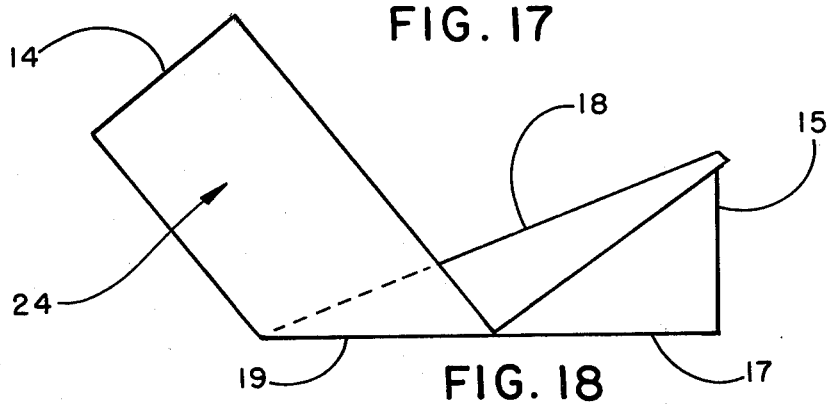
FIG. 18 is a side view of the FIG. 17 embodiment after folding.

Another variation may be obtained by adjusting the length of the anterior panel. As shown in FIGS. 17 – 18, as base point 20 is spaced farther inward from front edge 14, the anterior panel becomes greater in depth as measured from the front edge and when placed in position on the body is capable of covering more and more of the abdomen as well as completely covering the pubic area of the perineum. Such a structure is desirable for example when the device is used for infant or adult diapering.

As indicated in FIGS. 17 – 18, when base point 20 is moved rearwardly to create a larger anterior panel without changing other sheet dimensions, the first set of rearwardly diverging lines 18 may intersect the periphery of the sheet at back edge 15 rather than at side edges 16. A variation of this type does not change the broad functionality of the device and may be desirable where shorter structures are useful such as in the previously mentioned dribble cups adapted to receive and contain small dribbles, weeping, involuntary dripping or the like.

The protective device of this invention may be made available in either flat or pre-folded condition. When provided in flat condition, the fold lines should be permanently scored, embossed or indented to facilitate folding as the device is being readied for use. After folding a tape or other securement means is preferably provided and applied near the outer bottom folds as shown in the drawings.

Preferably the sheet material is prefolded for convenience to the user. In such event it is also preferably secured in its folded configuration by means of a tape 22, as shown in FIGS. 4 and 5, or by some other suitable securement means which does not interfere with the freedom of the posterior portion to move when in position on the body.

For some uses, as in the protection of garments from the staining which might otherwise be caused by light discharge, the device may comprise a single layer of material, and the material may be either absorbent or non-absorbent. When discharge is expected to be light, it may, for example, be comprised of a thin sheet of plastic film such as polyethylene, vinyl or the like which would serve primarily to shield but not absorb. However, for comfort the film may be coated with a thin fiber layer on the top surface which could also be absorbent.

For use as a drip catcher or dribble cup, the sheet material can be made of a thin plastic sheet with a thin layer or layers of absorbent material laminated to the top surface. Creped cellulose wadding tissues, non-woven webs, or thin air-formed and bonded batts are suitable for this purpose. Such structure is also suitable for menstrual use during light flow, or in conjunction with tampons, or for use in garment protection when a hemorrhoidal condition exists.

For menstrual use during normal or heavy flow, the sheet material may comprise a bottom fluid impermeable sheet, a central core of absorbent material of any desired thickness depending upon the absorbent capacity needed, and a thin top layer of fluid permeable material such as one of the non-woven fiber webs now in common use on catamenial pads. The top fluid permeable layer may be made of hydrophobic or hydrophilic fibers.

A similar multilayered structure is also suitable when the device is designed for diapering uses. The only major difference in the latter structure as compared to catamenial pads being the size of the starting sheet.

For general comfort purposes the width of the sheet is preferably in the range of 2 to 8 inches, the length of the pad being varied to accommodate the particular end use. However, greater widths may be used without seriously hampering the functionality.

Catamenial napkins, for example, may comprise a flat sheet size ranging from about 2 × 4 inches to about 6 × 10 inches.

Infant diapers may range in size from about 8 × 12 inches for newborns to about 8 − 14 × 20 inches for toddler's.

Geriatric diapers or adult incontinent garments may range in size from 8 − 14 × 20 inches to about 8 − 18 × 24 inches.

The diapers may be designed for use with a supporting garment to hold it in place or they may be made self-supporting and be used without a supplementary garment by adding pressure-sensitive tapes at the corners of one end, or by using pins or other fastening means, to secure the diaper around the waist.

It has been found that when used with snug-fitting garments such as panties or pantyhose of stretch material that catamenial napkins made in accordance with this invention usually will need no additional securement means to remain confortably in place. However, areas of pressure sensitive adhesive may be provided on the bottom side for securement if the supporting garment is not considered snug enough. Pressure sensitive adhesive may alternatively be provided on the top surface near the front and back edges for direct securement to the body.

While the preferred embodiments and specific examples depicted in the drawing show only an elongate rectilinear structure it is understood that the basic sheet material need not have a perimeter comprised of straight lines. The folded structure is equally applicable to sheet material with rounded corners and curved edges, and the terms generally elongate or generally rectangular are intended to include such forms.

What is claimed is:

1. A perineal shield and discharge containment device comprised of a sheet of flexible material in generally elongate form defined by a top body-contacting surface, a bottom surface, a front edge, a back edge and two side edges; said sheet being provided with a plurality of pre-established fold lines along which said sheet is folded prior to use;
    said lines comprising:
    a. a main fold line centrally and longitudinally disposed on said sheet and extending the full length of said sheet,
    b. a first pair of rearwardly diverging fold lines originating on said main fold line at a common point spaced from the front edge of said sheet, and said diverging fold lines extending from said point to the perimeter of said sheet,
    c. a second pair of rearwardly diverging fold lines disposed between said first pair of diverging lines and the side edges of said sheet, said second pair of lines also originating at said point on said main fold line and extending from said point to the perimeter of said sheet;
    said sheet being adapted for inward folding on said main fold line, outward folding on said first pair of rearwardly diverging fold lines, and inward folding on said second pair of rearwardly diverging fold lines.

2. The device of claim 1 wherein said sheet comprises a single layer of material.

3. The device of claim 2 wherein said sheet is pre-folded along the defined fold lines.

4. The device of claim 1 wherein said sheet comprises a single layer of material consisting of a fluid impervious film.

5. The device of claim 4 wherein said sheet is pre-folded along the defined fold lines.

6. The device of claim 1 wherein said sheet material comprises multi-layered material.

7. The device fo claim 1 wherein said sheet comprises two-layered material in which the top body-contacting surface layer is soft and fluid absorbent and the bottom surface layer is a fluid impervious film.

8. The device of claim 7 wherein said sheet is pre-folded along the defined fold lines.

9. The device of claim 1 wherein said sheet comprises a three-layered material in which the top body-contacting surface layer is fluid pervious, the intermediate layer comprises a batt of absorbent material, and the bottom surface layer is a fluid impervious sheet material.

10. The device of claim 9 wherein said sheet is prefolded along the defined fold lines.

11. The device of claim 10 wherein said device is a sanitary napkin.

12. The device of claim 1 wherein said sheet is prefolded along the defined fold lines.

13. The device of claim 1 wherein said device is prefolded along the defined fold lines and is secured in prefolded condition by securement means disposed adjacent said second pair of rearwardly diverging folds.

14. The device of claim 2 wherein said device is prefolded along the defined fold lines and is secured in prefolded condition by securement means disposed adjacent said second pair of rearwardly diverging folds.

15. The device of claim 4 wherein said device is prefolded along the defined fold lines and is secured in prefolded condition by securement means disposed adjacent said second pair of rearwardly diverging folds.

16. The device of claim 7 wherein said device is prefolded along the defined fold lines and is secured in prefolded condition by securement means disposed adjacent said second pair of rearwardly diverging folds.

17. The device of claim 9 wherein said device is prefolded along the defined fold lines and is secured by securement means disposed adjacent said second pair of rearwardly diverging folds.

18. The device of claim 17 wherein said device is a sanitary napkin.

19. The device of claim 9 wherein said device is a sanitary napkin.

20. The device of claim 9 wherein said device is a baby diaper.

21. The device of claim 9 wherein said device is an adult incontinent garment.

22. The device of claim 10 wherein said device is a baby diaper.

23. The device of claim 10 wherein said device is an adult incontinent garment.

24. The device of claim 17 wherein said device is a baby diaper.

25. The device of claim 17 wherein said device is an adult incontinent garment.

* * * * *